United States Patent [19]

Joly et al.

[11] Patent Number: 5,336,833
[45] Date of Patent: Aug. 9, 1994

[54] CATALYST BASED ON SILICA AND SULPHURIC ACID AND ITS USE FOR THE ALKYLATION OF PARAFFINS

[75] Inventors: Jean-Francois Joly, Paris; Christian Marcilly, Houilles; Eric Benazzi, La Celle Saint Cloud, all of France

[73] Assignee: Institut Francais Du Petrole, Rueil Malmaison, France

[21] Appl. No.: 966,648

[22] Filed: Oct. 26, 1992

[30] Foreign Application Priority Data

Oct. 25, 1991 [FR] France .................. 91 13303
Feb. 28, 1992 [FR] France .................. 92 02482

[51] Int. Cl.$^5$ .................................... C07C 2/62
[52] U.S. Cl. .................... 585/731; 502/216; 585/730; 585/723
[58] Field of Search ............ 585/723, 731, 730; 502/216

[56] References Cited

U.S. PATENT DOCUMENTS

| 2,276,250 | 2/1940 | Morrell | 585/731 |
|---|---|---|---|
| 2,430,803 | 11/1942 | Ciapetta | 585/731 |
| 2,987,774 | 4/1961 | Holzman | 585/731 |
| 3,922,319 | 11/1975 | Brockington | 585/731 |
| 3,970,721 | 7/1976 | Brockington et al. | 585/731 |
| 4,008,178 | 2/1977 | Brockington | 252/434 |
| 4,058,575 | 11/1977 | Cahn et al. | 585/731 |
| 4,148,758 | 4/1979 | Eberly, Jr. | 252/436 |

FOREIGN PATENT DOCUMENTS

| 0047540 | 7/1981 | European Pat. Off. . |
| 0259105 | 8/1987 | European Pat. Off. . |
| 0303005 | 5/1988 | European Pat. Off. . |

*Primary Examiner*—Asok Pal
*Attorney, Agent, or Firm*—Millen, White, Zelano & Branigan

[57] ABSTRACT

Impregnated catalyst based on silica and a solid state sulfuric acid and its use in the catalytic alkylation of isobutene and/or isopentane in the presence of at least one olefin having 3–6 carbon atoms per molecule. The catalyst may contain an additive, e.g., $B(OH)_3$, $HBF_4$, $H_3PO_4$, $FSO_3H$, $CF_3SO_3H$, $SbF_5$, $CF_3COOH$, and $SO_3$.

20 Claims, No Drawings

CATALYST BASED ON SILICA AND SULPHURIC ACID AND ITS USE FOR THE ALKYLATION OF PARAFFINS

BACKGROUND OF THE INVENTION

The present invention relates to a catalyst based on silica and sulphuric acid and its use in the catalytic alkylation of isobutane and/or isopentane by means of at least one olefin, which makes it possible to obtain at least one product e.g. in the group constituted by dimethyl butanes, trimethyl pentanes, trimethyl hexanes and trimethyl heptanes.

It is known that for the supply of internal combustion and controlled ignition engines and in particular those having a high compression ratio, it is particularly interesting to have high-octane fuels, i.e. essentially constituted by highly branched paraffin hydrocarbons. The alkylation of isoparaffins (isobutane and isopentane) b olefins containing 3 to 6 carbon atoms per molecule makes it possible to obtain such products. This reaction requires the use of very acid catalysts, with the aim of reducing unwanted reactions, such as olefin hydride extraction and polymerization reactions, which supply only slightly branched hydrocarbons with a low octane number and unsaturated hydrocarbons, cracking reactions and disproportionation reactions.

Existing processes for the production of hydrocarbons by the alkylation of isobutane by olefins use either sulphuric acid, or hydrofluoric acid as the catalyst. In these processes, the acid catalyst constitutes a liquid phase, which is contacted with the liquid olefin-isobutane mixture to form an emulsion. These processes are expensive and cause serious problems with regards to the safety of personnel and the environment. In order to obviate these problems, different catalytic systems of sulphuric and hydrofluoric acids in the liquid phase have been investigated.

In order to catalyze alkylation reactions of isoparaffins by olefins, a proposal has already been made to develop acid catalysts from numerous acid solids of various types. Among the families of acid catalysts, reference can be made to molecular sieves (cf. e.g. U.S. Pat. Nos. 3,236,762, 3,251,902, 3,644,565, 4,377,721, 4,384,161 and 4,300,015), macromolecular resins, optionally associated with $BF_3$ (cf. e.g. U.S. Pat. Nos. 3,855,342, 3,855,343, 3,862,258 and 3,879,489), per fluorine resins of the Nafion type (cf. e.g. U.S. Pat. Nos. 4,056,578 and 4,038,213) Lewis and/or Bronsted acids deposited on various inorganic supports (cf. e.g. U.S. Pat. Nos. 3,975,299, 3,852,371 and 3,979,476), chlorinated aluminas (cf. e.g. U.S. Pat. Nos. 3,240,840, 3,523,142, 3,607,859, 3,523,142, 4,066,716, 4,083,800 and 4,066,716) graphites intercalated by Lewis and/or Bronsted acids (cf. e.g. U.S. Pat. Nos. 4,083,885, 4,116,880, 4,128,596 and 3,976,714) and anions deposited on oxide supports such as $ZrO_2/SO_4$ (cf. e.g. JP-01288 329, JP-01245953 and JP-61242641). These solids lead to the production of branched isoparaffins, but suffering from several major defects, including the use of often very high isobutane/olefin molar ratios in order to limit the extent of secondary reactions and low stability in time of the catalytic activity (inhibition of the catalyst by the deposition of unsaturated oligomers), so that said catalysts frequently have to be regenerated. Moreover, the limited acidity of certain acid solids, such as e.g. molecular sieves, makes it necessary to use high reaction temperatures, which is prejudicial to the obtaining of high octane hydrocarbons.

SUMMARY OF THE INVENTION

In the present invention, a novel catalyst has been discovered making it possible to obtain paraffin compounds with high levels of branching and high octane numbers by the alkylation of isoparaffin (isobutane and/or isopentane) by at least one olefin having 3 to 6 carbon atoms per molecule. This novel catalyst is advantageously used in a process where the olefin and/or a mixture of olefins is introduced into the reactor in the liquid phase and mixed with the isoparaffin and/or the isoparaffin mixture. The catalyst is used in a solid, moving or fluid bed, or suspended in the liquid phase of the reagents subject to an effective stirring.

The catalyst according to the present invention contains silica and an acid phase comprising sulphuric acid, the silica being partly or totally impregnated by said acid phase. The sulphuric acid concentration is advantageously between 5 and 100% by weight, preferably between 50 and 100% by weight and in even more preferred manner between 88 and 100% by weight.

Numerous silica sources can be used. The specific surface of said silica is between 0.01 and 1500 $m^2/g$, preferably between 0.01 and 150 $m^2/g$ and in even more preferred manner between 0.01 and 50 $m^2/g$. The total pore volume of said silica is between 0.005 and 1.5 $cm^3/g$ and preferably between 0.005 and 1 $cm^3/g$. The silica can contain impurities such as e.g. oxides, alkalis, alkaline earths, aluminium compounds or any other known impurity, the total quantity of said impurities not exceeding 5 and preferably 2% by weight, based on the silica.

During the impregnation of said silica, the acid phase comprising the $H_2SO_4$ acid solution occupies a fraction of the total pore volume between 5 and 100%. The thus obtained catalyst is characterized by a specific surface between 0.01 and 500 $m^2/g$, preferably between 0.01 and 150 $cm^2/g$ and in even more preferred manner between 0.01 and 40 $m^2/g$.

It is possible to add to the acid phase at least one additive with a view to improving the catalytic performance characteristics. The additive is chosen from within the group formed by: $H_3PO_4$, $B(OH)_3$, $BF_4H$, $FSO_3H$, $CF_3COOH$, $SbF_5$, $CF_3SO_3H$ and $SO_3$.

In this case, during the impregnation of the silica, the acid phase comprising sulphuric acid and at least one additive occupies a fraction of the total pore volume of the silica between 5 and 100 and preferably between 60 and 90%. The thus obtained catalyst is characterized by a specific surface between 0.01 and 500 $m^2/g$, preferably between 0.01 and 150 $m^2/g$ and in even more preferred manner between 0.01 and 40 $m^2/g$.

An even more preferred additive according to the present invention is sulphur trioxide $SO_3$. When the latter is used, the acid phase incorporating at least the sulphuric acid and the sulphur trioxide is often referred to as "oleum". The sulphur trioxide weight content in the oleum used is between 0.01 and 60% and preferably between 1 and 30%. When said oleum is used for impregnation, it is preferable to add to said oleum a supplementary additive with a view to increasing the acidity of the catalyst and therefore improve the catalytic performance characteristics thereof. The preferred supplementary additive is boric acid ($H_3BO_3$), the boric acid weight content within the mixture comprising the sulphuric acid and the sulphur trioxide advantageously being between 0.01 and 50% and in even more preferred manner between 0.01 and 10%.

The preparation process of the catalyst according to the invention comprises two stages. In a first stage the silica is calcined at a temperature exceeding 50° C., preferably exceeding 80° C. and in even more preferred manner between 200° and 600° C., e.g. at approximately 500° C. The duration of said calcination stage is normally between 10 minutes and 50 hours. Calcination can be carried out in the presence of air or an air/nitrogen mixture with a flow rate between 0.001 and 10 l/h/g. The second stage consists of the impregnation of said calcined silica by the acid phase. In order to carry out this stage, it is possible to use all known procedures. When kept at a temperature below the melting point of said acid phase and protected from moisture, the catalyst according to the invention thus contains solid acid phase-impregnated silica.

The catalyst according to the present invention is used in the pure state or diluted with various materials having little catalytic activity in the considered reaction, such as e.g. silica, alumina, magnesia or various clays such as e.g. bentonite, montmorillonite or kaolin.

The isoparaffin-olefin mixture is introduced into the reactor at a space velocity, expressed as olefin weight introduced per weight unit of catalyst and per hour is between 0.001 and 10 $h^{-1}$ and preferably between 0.002 and 2 $h^{-1}$. The mixture can also be formed within the reactor. In all cases, the thus formed mixture is in the reactor under pressure and temperature conditions such that the hydrocarbon mixture remains liquid on the catalyst and the constituents of the catalyst remain in the solid state.

The reaction temperature can be between −50° and 150° C., but we have surprisingly discovered that the catalytic performance characteristics are greatly improved when the reaction temperature is below the crystallization temperature of the acid phase used for impregnating the silica. The reaction temperature must then be below +6° C., preferably at 0° C., more preferably below −5° C. and even more preferably below −10° C. The reactor pressure is adequate to maintain the hydrocarbons in the liquid state in the reactor.

One of the advantages of the catalyst according to the invention when the acid phase is mainly constituted by sulphuric acid is the possibility of alkylating isobutane and/or isopentane at temperatures below −10° C. and which can reach −30° C. Thus, L. F. Albright et al. in Ind. Eng. Chem. Res. 1988, 27, pp. 381–397 very clearly indicate the interest of carrying out isobutane alkylation in the presence of sulphuric acid at temperatures below 0° C., namely a very significant reduction in secondary reactions and therefore the consumption of the catalyst, whilst improving the quality of the hydrocarbons obtained. The published results only refer to tests carried out on a laboratory scale. The disadvantage associated with the use of such temperatures is the necessity of extremely powerful stirring, in view of the very high viscosity of the sulphuric acid in solution at such temperatures, with even an impossibility of stirring if the temperature is below the melting point of sulphuric acid. The catalyst according to the invention makes it possible to carry out the alkylation of isobutane and/or isopentane at these very low temperatures without any need for increasing the power of the stirring, the sulphuric acid phase being contained within the porosity of the silica.

In order to limit the secondary reactions, it is possible to use an isoparaffin excess compared with the olefin. For example, in the case of the alkylation of isobutane by a butene, the isobutane can be introduced in the pure state into the charge or in the form of a mixture of butanes e.g. containing at least 40% of isobutane. Moreover, it is possible to introduce a pure butene or a mixture of isomeric butenes. In all cases, the molar isobutane/butene ratio in the charge is between 1 and 100, preferably between 3 and 50 and in even more preferred manner between 5 and 10. The reaction products can be regularly controlled by measuring the bromine number, e.g. in accordance with draft French standard Pr. M. 07.071 of March 1969.

When the nature of the catalyst and the catalyst operating conditions are carefully chosen (particularly the temperature), the catalyst according to the invention makes it possible to produce products for the alkylation of paraffins by olefins, which are of interest as fuels for engines and petrol constituents and which e.g. comprise at least 60 molar % paraffins having 8 carbon atoms per molecule and less than 1 molar % of unsaturated compounds, the paraffins having 8 carbon atoms per molecule with 70 to 98 molar % of trimethyl pentanes.

Another advantage of the catalyst according to the invention is the possibility of low temperature alkylation of isobutane with mixtures of olefins having 3 to 6 carbon atoms per molecule, where the proportion of olefins having at least 5 carbon atoms per molecule is very high (at least 10 and preferably at least 40% by weight).

The following examples illustrate the invention without limiting its scope.

EXAMPLE 1

(according to the invention): Sulphuric acid catalyst on silica

Preparation of catalyst A 16 g of macroporous silica with a specific surface of 27 $m^2/g$ and a total pore volume of 0.78 $cm^3/g$ are activated by calcination in air for 4 hours at 500° C. The thus activated silica is kept under argon. This is followed by the dry impregnation of 14 g of said silica by 20 g of a 96% by weight sulphuric acid solution. The thus obtained solid, called catalyst A, contains 20 g of sulphuric acid and 14 g of silica and is kept under argon at −18° C.

Alkylation of isobutane by 1-pentene 34 g of catalyst A prepared according to the aforementioned method is introduced into a Fischer & Porter-type glass reactor with a volume of 360 ml and previously purged under an argon flow. The reactor containing the catalyst A is then sealed, placed under an initial vacuum and then cooled to −20° C. 80 $cm^3$ of isobutane are then added to the reactor containing the catalyst accompanied by stirring, said reactor being immersed in a cold bath at −20° C. The catalyst A+isobutane system is kept stirred for 30 minutes in order to render the temperature uniform. There is a regular addition of 1.73 $cm^3$ of 1-pentene per hour for a total time of 12 hours, the reactor temperature being maintained at −12° C. for the entire injection period.

Following the reaction, the hydrocarbon phase is removed from the reactor and then the isobutane is slowly evaporated, followed by the collection of the alkylate, which is analysed by gas chromatography. Its weight composition is given in the following Table 1. The olefin conversion is 100%.

TABLE 1

| | |
|---|---|
| $iC_5$ | 3.20 |
| $C_6$ | 2.65 |
| $C_7$ | 0.88 |
| $C_8$ | 11.70 |
| $C_9$ | 75.40 |
| $C_9^+$ | 6.17 |

The $C_8$ fraction contains 90.3% by weight of trimethyl pentanes and the $C_9$ fraction 90.8% of trimethyl hexanes.

Alkylation of isobutane by an olefin $C_4$–$C_6$ fraction

Use is made of a catalyst prepared in the same way as catalyst A described hereinbefore for the alkylation of isobutane by an olefin $C_4$–$C_6$ fraction. The fraction used has the following composition.
10% 2-butene
35% 1-pentene
55% hexenes.

The hexene fraction contains 60% of 2-methyl-2-pentene and 40% of 2-hexene.

The previously described procedure is used for the alkylation reaction and 90 ml of isobutane are alkylated by 7.4 ml of the olefin charge described hereinbefore for 4½ hours at a temperature of $-15°$ C. The alkylate is collected and analysed by gas chromatography. There is a total conversion of the olefins. The weight composition of the alkylate obtained is given in the following Table 2.

TABLE 2

| | |
|---|---|
| $iC_5$ | 3 |
| $C_6$ | 18 |
| $C_7$ | 3 |
| $C_8$ | 25 |
| $C_9$ | 25 |
| $C_9^+$ | 26 |

The $C_6$ fraction contains 73% of methyl pentanes, the $C_8$ fraction 92% by weight of trimethyl pentanes and the $C_9$ fraction contains 89% of trimethyl hexanes.

EXAMPLE 2

(according to the invention): Sulphuric acid catalyst on silica

Preparation of catalyst B 15 g of macroporous silica with a specific surface of 27 m²/g and a total pore volume of 0.78 cm³/g are activated by calcination in air for 2 hours at 500° C. The thus activated silica is kept under argon. This is followed by the dry impregnation of 13.7 g of said silica by 18.96 g of a 96% by weight sulphuric acid solution. The thus obtained solid, called catalyst B, contains 18.96 g of sulphuric acid and 13.7 g of silica and is kept under argon at $-20°$ C.

Alkylation of isobutane by 1-butene 32 g of catalyst B prepared according to the method described hereinbefore are introduced into a Fischer & Porter-type glass reactor with a volume of 360 ml and previously purged under an argon flow. The reactor containing catalyst B is then sealed, placed under an initial vacuum and cooled to $-20°$ C. 57 cm³ of isobutane are then added to the reactor containing the catalyst and accompanied by stirring, said reactor being immersed in a cold bath at $-20°$ C. The catalyst B+isobutane system is kept under stirring for 30 minutes, in order to render the temperature uniform. There is a regular addition of 1.70 cm³ of 1-butene/hour for a total period of 6 hours, the reactor temperature being maintained at $-7°$ C. for the duration of the injection.

Following the reaction, the hydrocarbon phase is removed from the reactor and then the isobutane is slowly evaporated and the alkylate collected, which is analysed by gas chromatography. Its weight composition is given in the following Table 3. The olefin conversion is 100%.

TABLE 3

| | |
|---|---|
| $iC_5$ | 1.26 |
| $C_6$ | 3.16 |
| $C_7$ | 2.62 |
| $C_8$ | 83 |
| $C_9$ | 1.70 |
| $C_9^+$ | 8.26 |

The $C_8$ fraction contains 89.7% by weight trimethyl pentanes and the $C_9$ fraction 92.2% of trimethyl hexanes.

EXAMPLE 3

(according to the invention): Sulphuric acid catalyst+sulphur trioxide on silica Preparation of catalyst C 14 g of macroporous silica with a specific surface of 27 m²/g and a pore volume of 1 cm³/g are activated by calcining in air for 4 hours and at 500° C. The thus activated solid is kept under argon. This is followed by the dry impregnation of 10 g of the calcined solid by 7 cm³ of the mixture constituted by 80% by weight sulphuric acid (99.99%) and 20% by weight sulphur trioxide. The thus obtained catalyst C contains 13.5 g of oleum and 10 g of silica and is kept under an argon atmosphere at $-18°$ C.

Alkylation of isobutane by 1-butene using catalyst C 20 g of catalyst C prepared according to the method described in Example 3 are introduced into a Fischer & Porter-type glass reactor with a volume of 360 cm³ and previously purged under an argon flow. The reactor containing the catalyst is then sealed and placed under an initial vacuum, followed by cooling at $-20°$ C. 72 cm³ of isobutane are then added to the reactor containing the catalyst, accompanied by stirring, said reactor being immersed in a cold bath at $-20°$ C. Stirring is maintained of the catalyst+isobutane system for 30 minutes in order to render the temperature uniform. There is a regular addition of 50 cm³ of a mixture constituted by 24 volume % of 1-butene and 76 volume % of isobutane for a total period of 10 hours, the reactor temperature being maintained at $-15°$ C. throughout the injection period.

After reaction, the hydrocarbon phase is removed from the reactor and the isobutane slowly evaporated. The alkylate is collected and analysed by gas chromatography, its weight composition being given in Table 4.

TABLE 4

| | |
|---|---|
| $iC_5$ | 1.5 |
| $C_6$ | 1.1 |
| $C_7$ | 1.9 |
| $C_8$ | 90 |
| $C_9$ | 1.2 |

TABLE 4-continued

| | |
|---|---|
| $C_9^+$ | 4.3 |

The olefin conversion is 98%. The alkylation yield is 200%, based on the transformed olefin. The $C_8$ fraction contains 89% by weight of trimethyl pentanes.

EXAMPLE 4

(according to the invention): Preparation of a sulphuric acid catalyst+sulphur trioxide+boric acid on silica

Preparation of catalyst D

For the preparation of catalyst D use is made of 13 g of the same macroporous silica as that used for the preparation of catalyst C, the calcination conditions being identical. Preparation takes place of a mixture constituted by oleum and boric acid and for this purpose use is made of 7 cm³ of the same mixture as that used for obtaining catalyst C and to which is added 0.81 g of anhydrous boric acid. This gives 14.31 g of a mixture of sulphuric acid (75.47% by weight), sulphur trioxide (18.86% by weight) and boric acid (5.67% by weight).

This is followed by the dry impregnation of 11 g of calcined silica by all the mixture described hereinbefore. The thus obtained catalyst D contains 14.31 g of acid phase and 11 g of silica and is kept under an argon atmosphere at $-18°$ C.

Alkylation of isobutane by 1-butene using catalyst D

The catalytic test of alkylating isobutane by 1-butene is repeated under the same experimental conditions as those described in Example 3 and the results are given in the following Table 5.

TABLE 5

| | |
|---|---|
| $iC_5$ | 0.8 |
| $C_6$ | 0.5 |
| $C_7$ | 1.1 |
| $C_8$ | 94.6 |
| $C_9$ | 0.9 |
| $C_9^+$ | 2.1 |

The alkylation yield is 201%, based on the transformed olefin. The $C_8$ fraction contains 92% by weight trimethyl pentanes.

This table shows the interest of adding boric acid to the mixture of sulphuric acid and sulphur trioxide and this represents one of the preferred embodiments of the invention.

We claim:

1. Catalyst comprising silica and an acid wherein the acid comprises between 5% and 100% by weight of sulfuric acid, and wherein the acid is in a solid phase state in the silica, the silica having been calcined and then impregnated by said acid and having a specific surface between 0.01 and 1500 m²/g and a total pore volume of between 0.005 and 1.5 cm³/g, the acid occupying between 5% and 100% of the total pore volume.

2. Catalyst according to claim 1, wherein the silica, prior to impregnation by the acid, contains at the most 5% impurities.

3. Catalyst according to claim 1, wherein the acid also contains at least one additive.

4. Catalyst according to claim 3, wherein the additive is $B(OH)_3$, $HBF_4$, $H_3PO_4$, $FSO_3H$, $CF_3SO_3H$, $SbF_5$, $CF_3COOH$ or $SO_3$.

5. Catalyst according to claim 3, wherein the additive is sulphur trioxide $SO_3$, the sulphur trioxide weight content in said acid being between 0.01 and 60%.

6. Catalyst according to claim 3, wherein the acid contains sulphuric acid, sulphur trioxide and boric acid, the sulphur trioxide weight content in said acid phase being between 0.01 and 60% and the boric acid weight content in the mixture comprising sulphuric acid and sulphur trioxide being between 0.01 and 50%.

7. A catalyst according to claim 2, wherein the sulfuric acid and the additive comprise between 60% and 90% of the total pore volume.

8. A catalyst according to claim 7, wherein the sulfuric acid concentration is 88–100% by weight.

9. A catalyst according to claim 1, wherein the silica has a specific surface of between 0.01 and 150 m²/g.

10. A catalyst according to claim 1, wherein the silica has a specific surface of between 0.01 and 50 m²/g, and the total pore volume is between 0.005 and 1 cm³/g.

11. A catalyst according to claim 1, wherein the sulfuric acid concentration is 88–100% by weight.

12. In a process for the catalytic alkylation of at least one of isobutane and isopentane with at least one olefin having 3–6 carbon atoms per molecule, the improvement which comprises employing a catalyst comprising silica and an acid wherein the acid comprises between 5% and 100% by weight of sulfuric acid and wherein the acid is in a solid phase state in the silica, the silica having been calcined and then impregnated by said acid and having a specific surface between 0.01 and 1500 M²/g and a total pore volume of between 0.005 and 1.5 cm³/g, the acid occupying between 5% and 100% of the total pore volume.

13. A process according to claim 12, wherein the reaction temperature is below 0° C.

14. A process according to claim 12, wherein the silica, prior to impregnation by the acid, contains at the most 5% impurities.

15. A process according to claim 12, wherein the acid also contains at least one additive.

16. A process according to claim 12, wherein the sulfuric acid concentration in the catalyst is 88–100%.

17. A process according to claim 13, wherein the sulfuric acid concentration in the catalyst is 88–100%.

18. The process of claim 12, wherein the catalyst is used in a moving bed.

19. The process of claim 12, wherein the catalyst is used in a fluid bed.

20. The process of claim 12, wherein the catalyst is used suspended in a liquid phase of the reagents.

* * * * *